(12) United States Patent
Figueroa et al.

(10) Patent No.: US 8,609,198 B2
(45) Date of Patent: Dec. 17, 2013

(54) PHARMACEUTICAL DOSE FORM WITH A PATTERNED COATING AND METHOD OF MAKING THE SAME

(75) Inventors: Iddys D. Figueroa, Dorado, PR (US); Enrique C. Abreu, Mayaguez, PR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 3025 days.

(21) Appl. No.: 10/896,301

(22) Filed: Jul. 21, 2004

(65) Prior Publication Data

US 2006/0018969 A1 Jan. 26, 2006

(51) Int. Cl.
*B05D 1/40* (2006.01)
*A61K 9/48* (2006.01)
*A61K 9/28* (2006.01)
*A61K 9/30* (2006.01)
*A61K 9/38* (2006.01)
*B05D 1/02* (2006.01)
*B05D 5/00* (2006.01)
*B05D 1/04* (2006.01)

(52) U.S. Cl.
USPC .......... 427/479; 424/463; 424/474; 424/475; 424/482; 427/427.4; 427/457; 427/458; 427/475; 427/477

(58) Field of Classification Search
USPC .............. 106/122; 424/463, 489; 118/13
See application file for complete search history.

(56) References Cited

U.S. PATENT DOCUMENTS

| | | | |
|---|---|---|---|
| 3,688,804 A * | 9/1972 | Brown et al. | 139/1 R |
| 3,957,523 A | 5/1976 | Ohno et al. | |
| 3,981,984 A | 9/1976 | Signorino | |
| 4,133,290 A * | 1/1979 | Melliger | 118/668 |
| 4,322,449 A * | 3/1982 | Voss et al. | 427/2.14 |
| 4,533,562 A * | 8/1985 | Ikegami et al. | 427/2.18 |
| 4,548,825 A * | 10/1985 | Voss et al. | 426/383 |
| 5,026,709 A * | 6/1991 | Harwood et al. | 514/263.34 |
| 5,110,599 A | 5/1992 | Anhäuser et al. | |
| 5,204,055 A | 4/1993 | Sachs et al. | |
| 5,529,767 A | 6/1996 | Brox et al. | |
| 5,578,316 A * | 11/1996 | Bhardwaj et al. | 424/441 |
| 5,609,908 A | 3/1997 | Voss | |
| 5,992,742 A * | 11/1999 | Sullivan et al. | 235/462.01 |
| 6,086,942 A | 7/2000 | Carden, Jr. et al. | |
| 6,623,785 B2 | 9/2003 | Childers | |
| 6,698,868 B2 * | 3/2004 | Trueba et al. | 347/63 |
| 2002/0197388 A1 | 12/2002 | Brown et al. | |
| 2003/0099708 A1 | 5/2003 | Rowe et al. | |
| 2003/0143268 A1 | 7/2003 | Pryce Lewis et al. | |
| 2004/0175331 A1* | 9/2004 | Figueroa et al. | 424/45 |

FOREIGN PATENT DOCUMENTS

WO WO 03/026628 A2 * 4/2003 ............ A61K 9/28

OTHER PUBLICATIONS

Website reference: www.fischersci.com; compound reference for polyethylene glycol (PEG) 400.*
Handbook of Pharmaceutical Excipients (1988); p. 251: Shellac.*
Website reference: www.fischersci.com; compound reference for polyethylene glycol (PEG)400.*
Remington: The Science and Practice of Pharmacy (19th Ed.); edited by Gennaro; (1995); p. 884 (Titanium dioxide).*
Kastra et al. "Oral dosage forms fabricated by Three Dimensional Printing" J. of Controlled Release; 66 (2000), pp. 1-9.*
Website: Wikipedia search for "femtoliter": http://en.wikipedia.org/wiki/Femtoliter.*

* cited by examiner

*Primary Examiner* — Robert A Wax
*Assistant Examiner* — Jeffrey T Palenik

(57) ABSTRACT

A method for producing a pharmaceutical dose form includes depositing a measured quantity of a first coating material on an external surface of the dose form in a patterned configuration. A measured quantity of a second coating material is deposited on the surface of the dose form in a patterned configuration in relationship to the first coating material. The first and second coating materials form a coating layer in overlying relationship with at least a portion of the external surface of the dose form.

20 Claims, 3 Drawing Sheets

PHARMACEUTICAL DOSE FORM WITH A PATTERNED COATING AND METHOD OF MAKING THE SAME

BACKGROUND

The disclosure herein relates to methods for coating substrates and coated substrates formed thereby. The coated substrates may be tablets or other forms for pharmaceutical use.

The need for controlled release and/or delayed release of pharmaceuticals arises in many instances and treatment protocols. The efficacy and uptake of various pharmaceutical compounds is enhanced in situations where the release or dissolving of the compound may be delayed to occur at a specific anatomical location and/or time interval. Additionally, the efficacy of certain pharmaceutical compounds is enhanced or regulated by the slow release of the compound or compounds over time. Various strategies have been developed for producing time-release pharmaceutical materials. Also, various strategies have been proposed for providing delayed release dose forms in which the active pharmaceutical agent is not released for uptake in the body until the dose form reaches a certain anatomical location. Thus, various coatings have been proposed for providing tablets that dissolve in the stomach, intestine, or other region.

Attempts have been made to produce a coated tablet or dose form that provides delayed dissolution over time. Some of these attempts include the random application of multiple coating compounds having different dissolution characteristics. In such instances, the coating compound is insoluble in a material, such as gastrointestinal fluid, and is doped with a soluble polymer such that the soluble polymer in the coating composition may selectively dissolve once the tablet reaches the stomach, thereby forming pores and initiating medication release. The coating process typically involves spray application of a solution containing the dissolved polymers over a drug core. The amount of pore formation and its position is a stochastic process. Thus, the number and density of potential pore locations may vary from dose form to dose form and from pharmaceutical batch to pharmaceutical batch.

SUMMARY

A method for producing a pharmaceutical dose form includes depositing a measured quantity of a first coating material on an external surface of the dose form in a patterned configuration. A measured quantity of a second coating material is deposited on the surface of the dose form in a patterned configuration in relationship to the first coating material. The first and second coating materials form a coating layer in overlying relationship with at least a portion of the external surface of the dose form.

DESCRIPTION OF THE DRAWINGS

Objects, features, and advantages of embodiments of the present invention will become apparent by reference to the following detailed description and drawings in which like reference numerals correspond to similar, though not necessarily identical, components. For the sake of brevity, reference numerals having a previously described function(s) may not necessarily be described in connection with subsequent drawings in which they appear.

DETAILED DESCRIPTION OF THE EMBODIMENTS

Disclosed herein is a method for producing a pharmaceutical dose form having a coated surface in which a measured quantity of a first coating material is deposited on the surface of the dose form in a patterned configuration. In an embodiment, a measured quantity of a second coating material is deposited on the surface of the dose form in a patterned configuration in relationship to at least a portion of the deposited first coating material. The dose form resulting from the process is one which has a coating layer composed of at least two distinct coating materials with at least one of the coating materials being positioned at a substantially precise location on the dose form surface. The two distinct coating materials may have different characteristics (for example, dissolution characteristics) from one another such that one of the coating materials dissolves after contact with the desired environment, such as gastrointestinal fluid and/or the like. The dissolution of at least one deposited coating material results in the formation of pores in the coating layer. The pores have substantially precisely defined location, size, and/or configuration suitable for providing measured release of at least a portion of one or more active pharmaceutical compound(s) contained in the dose form.

It is to be understood that the term "dose form" is to be interpreted in a broad sense as including a wide variety of pharmaceutical products. Thus, it is contemplated as being with the purview of the embodiment(s) of the present invention that "dose form" includes pharmaceutical products to be taken orally, for example, pharmaceutical tablets of conventional shape, as well as capsules, spherules and tablets of unconventional shape. It is to be understood that the pharmaceutical substrate making up the dose form may be a conventional tablet core or may be, for example, an edible sheet or film. It is to be understood that "dose form" also covers pharmaceutical products not taken orally, for example a pessary, a bougie, a suppository, or a patch for application to the skin.

Where reference is made to "pharmaceutical substrate," it is to be understood that the term includes substances of the dose forms indicated above. The term "dose form" does not, however, include pharmaceutical products such as small pellets and granules, for example small pellets which are filled into capsule shells for administration, and granules which are composed to form tablets. Such pellets or granules are not themselves each dose forms but rather, when combined into a capsule or tablet define a dose form. It is contemplated that the embodiments may find particular application to pharmaceutical tablets having conventional shapes. Where reference is made through the specification to pharmaceutical tablets, it is to be understood that this should be interpreted in a broad sense, unless it is clear to the contrary, as covering other pharmaceutical products taken orally, for example, capsules, spherules and the like.

It is to be understood that the term "active material" and/or "active component" used throughout the specification includes materials that are biologically active and may comprise one material or a mixture of pharmaceutical materials. The pharmaceutical materials include those materials that are administered for the prevention and/or treatment of disease(s). Additionally, pharmaceutical materials may include palliative agents administered for the treatment of pain and the like.

In conventional methods of producing pharmaceutical tablets, a mixture containing the biologically active ingredient(s) is formulated together with appropriate diluents and inert ingredients. Portions of the resulting mixture are formed into discrete tablets by various methods, such as pressing samples of the mixture. It is also contemplated that pharmaceutical tablets may be produced in which the biologically active agent is more substantially precisely located within the geometry of the tablet. Thus, the pharmaceutically active agent may be located in a region of the tablet, such as in a layer and/or a quadrant of the respective tablet. It is also contemplated that the tablet may include a multilayer core and/or other appropriate geometric configurations.

Figure 1:
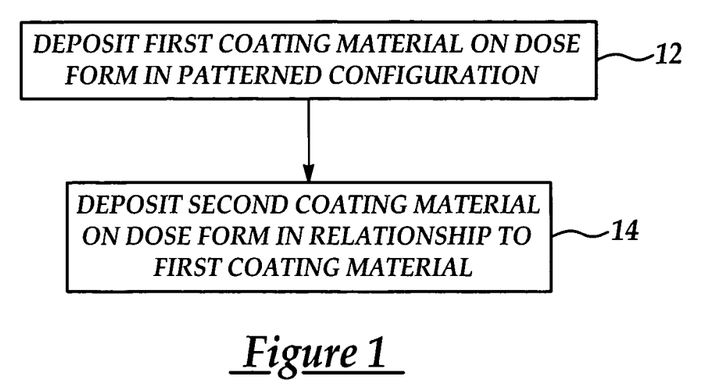
FIG. 1 is a process flow chart of an embodiment of the method of the present invention.

As broadly construed, an embodiment of the method for preparing a pharmaceutical dose form is outlined in FIG. 1. As shown, a first coating material is deposited on the external surface of a dose form in a patterned configuration, as at reference numeral 12, and a second coating material is deposited on the surface of the dose form in relationship to at least a portion of the first coating material, as at reference numeral 14.

Figure 2:
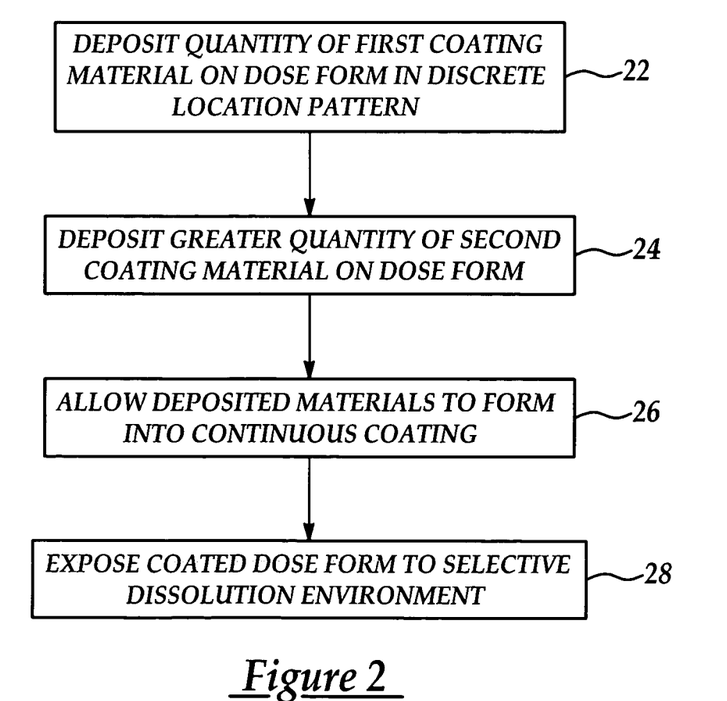
FIG. 2 is a process flow chart of an alternate embodiment of the method of the present invention.

FIG. 2 outlines a more detailed view of an embodiment of the method for preparing a dose form. This embodiment of the method includes the deposition of a quantity of a first coating material in discrete separate volumes on a predetermined location of the surface of the dose form, as at reference numeral 22. The method further includes depositing on the dose form a greater amount of a second coating material than the first coating material, shown at reference numeral 24; allowing the materials to form a contiguous coating, shown at reference number 26; and then exposing the dose form to a selective dissolution environment, shown at reference numeral 28.

Figure 3:
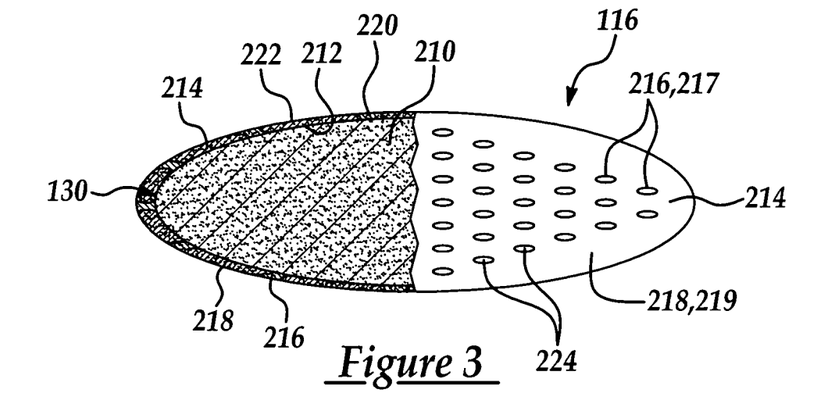
FIG. 3 is a cutaway partial cross sectional view of an embodiment of the controlled release dose form of the present invention.
Figure 4:
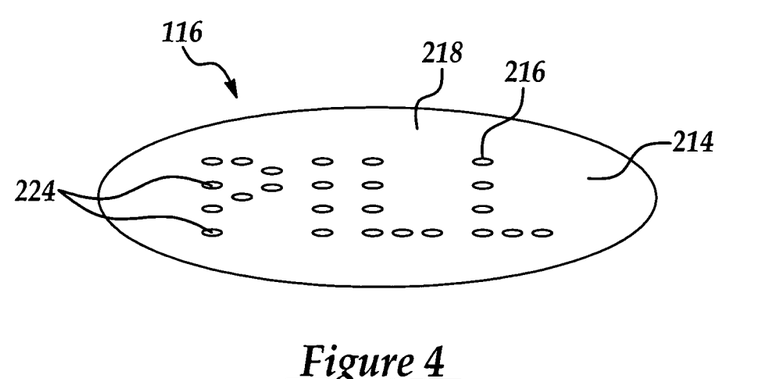
FIG. 4 is a plan view of an alternate embodiment of a dose form of the present invention having identifying indicia disposed thereon.
Figure 5:
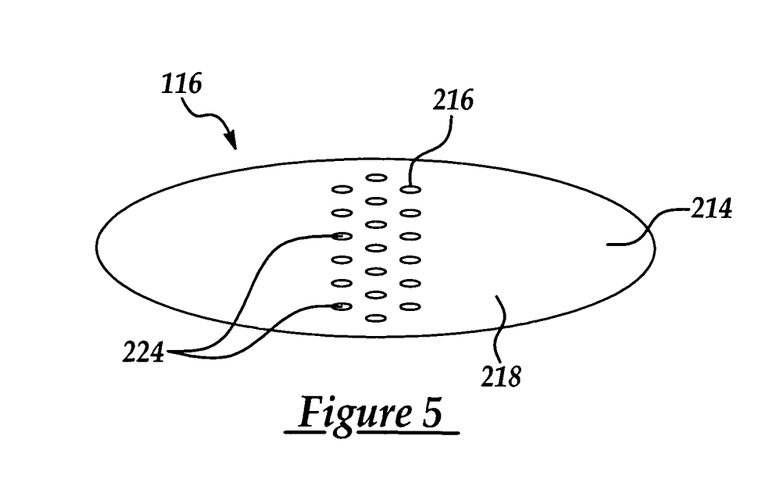
FIG. 5 is a plan view of an alternate embodiment of a dose form of the present invention having a patterned covering layer for rapid delayed dissolution.

These and further embodiments of the method and the dose form are discussed in detail in reference to FIGS. 3 through 5.

Referring now to FIG. 3, an embodiment of a dose form 116 having controlled release characteristics is depicted. The dose form 116 includes an internal region 210 containing at least one active pharmaceutical component. The internal region 210 may also include various inert ingredients, binders, and/or the like. The active pharmaceutical component may be dispersed or admixed within the inert material. Alternatively, it is also contemplated that the internal region 210 may be stacked, layered, and/or otherwise configured.

The internal region 210 has an outer surface 212 adapted to receive a suitable coating layer 214 in overlying relationship thereon. The coating layer 214 may be composed of at least two coating materials in contiguous relationship to one another.

In an embodiment of the method of forming a dose form 116, a first coating material 216 is deposited on the external surface 130 of a dose form 116 in a patterned configuration. This is followed by the deposition of a second coating material 218 in relationship to at least a portion of the first coating material 216 and the surface 130 of the dose form 116. The first and second coating materials 216, 218 may be any suitable materials capable of spray application and may be composed of compounds typically classified as suitable for human use and/or consumption.

It is contemplated that the first coating material 216 may be a fluid composition capable of being used in a suitable electronic fluid ejection device application. The second coating material 218 may be a liquid capable of similar application and may have at least one physical characteristic different from the first coating material 216. The characteristic that differs between the first and second coating materials 216, 218 may be a dissolution characteristic, which affects the solubility of the respective coating materials 216, 218 in a defined environment. Non-limiting examples of dissolution characteristics include at least one of solubility at a defined pH range, solubility at a defined temperature range, solubility at a defined pressure, and/or solubility at a defined time interval of exposure to one of the foregoing conditions.

In one embodiment of the method, it is contemplated that first and second coating materials 216, 218 may be selected based upon performance in a suitable target defined environment. Where delayed dissolution of a coating configuration is desired, it is contemplated that the first coating material 216 may be one capable of sufficient dissolution or solubilization at a pH typical for the defined environment desired, e.g. The gastrointestinal tract, digestive tract, the pulmonary system, the vagina, the rectum, the eyes, the blood system, etc., while the second coating material may be one exhibiting significant insolubility at that typical pH.

As used herein, the term "defined environment" may be construed as an anatomical region or condition into which the pharmaceutical dose form 116 is introduced or migrates. One non-limiting example of an anatomical region or condition is the stomach region of a gastrointestinal tract. The stomach region is typically characterized by the presence of a gastric solution having a defined pH in the acidic range. The pH in the stomach ranges between about 1 and about 3. The pH in the different parts of the small intestine (duodenum, jejunum and ileum) is a more neutral to basic pH, ranging between about 6 and about 7.5-8 (e.g. in the duodenum, pH ranges between about 6 and about 6.5). The pH in the large intestine ranges between about 5 and about 6. It is to be understood that these pH ranges are illustrative and not intended to be limiting, as the pH in various defined environments may vary.

In an embodiment, it is contemplated that at least one of the applied coating materials 216, 218 will have a dissolution characteristic that permits the coating material to dissolve at the pH range found in the stomach region. Further, more than one applied coating material 216, 218 may have a dissolution characteristic that permits the respective coating material to dissolve at different rates in the anatomical region or condition.

In an embodiment, the coating materials 216, 218 form at least two distinct coating regions 217, 219 formed of two materials 216, 218 having dissolution characteristic(s) distinct from one another. The distinct coating regions 217, 219 each have an inner surface proximate to the internal region 210 of the dose form 116 and an opposed outer surface 220, 222, respectively. Exposure to a given dissolution media (not shown) selectively dissolves the material 216 in coating region(s) 217 leaving a plurality of open pores/porous opening(s) 224 in the coating layer 214, thereby exposing the internal region 210 for controlled release through the pores 224. It is to be understood that the pore(s) 224 may also permit contact between the dissolution environment and the active material contained in the dose form 116 and/or facilitate removal of the remaining applied coating material.

It is to be understood that the discrete portions of the first polymeric material 216 may be deposited at volumes sufficient to permit surface coating at the targeted/defined locations on the dose form surface 130. The locations may be determined by a suitable control algorithm and/or other suitable control mechanism. It is contemplated that the discrete amounts of the first coating material 216 may be deposited at volumes ranging between about 1 femtoliter and about 500 picoliters. If desired, the targeted discrete location may receive multiple droplets in order to provide desired pore 224 size in the coating material region 217 of the dose form 116.

However, as broadly construed, embodiments of the method include the application of a measured lesser quantity of the first coating material 216 at a plurality of discrete locations on the surface 130 of the dose form 116 in a patterned configuration. This may be followed by the application of a measured quantity of a second coating material 218 on the surface 130 of the dose form 116 in a patterned configuration in relationship with at least a portion of the applied first coating material 216 such that a pattern of the respective first and second coating 216, 218 forms a continuous solidified coating layer 214 on the surface 130 of the dose form 116. The resulting coated dose form 116 may then be stored or processed further as desired and/or required. Further processing may include, but is not limited to, appropriate quality assurance procedures, indicia marking, and/or the like.

It is to be understood that the first coating material 216 may be applied and/or deposited in a predetermined pattern. The predetermined pattern may be any suitable random and/or non-random configuration. Thus, it is contemplated that the first coating material 216 may be located at a single area on the dose form 116, or may be placed in spaced patterned relationship on one or more areas of the dose form 116. The predetermined pattern may be one that uniformly positions discrete portions or quantities of the first coating material 216 on the surface 130 of the dose form 116. Alternately, the predetermined pattern may be one that achieves a pattern or indicia of the first coating material 216 on at least one region 217 of the dose form 116 (see FIG. 4). It is also contemplated that the predetermined pattern may be one that facilitates "unzipping" of the associated dose form in a manner described herein. Other predetermined patterns are contemplated as desired and/or necessitated depending on factors that may include, but are not limited to, desired drug delivery location and uptake, dissolution environment, and/or the like.

It is to be understood that the quantity of first coating material 216 deposited in a patterned relationship on the surface 130 of the dose form 116 may constitute a minor portion (less than or equal to about 50 percent of the total dose form coating material 214) of the total dose form coating 214. Once the quantity of the first coating material 216 has been deposited, a quantity (for non-limitative example, a greater quantity) of a second coating material 218 may be deposited on the dose form 116. The second coating material 218 may be applied/deposited to target locations on the dose form 116 in any manner that permits substantially contiguous contact with deposited regions 217 of the first coating material 216 such that a continuous coating layer 214 is formed. It is contemplated that the second coating material 218 may be applied/deposited sequentially or substantially simultaneously with the quantity of first coating material 216.

The first and second coating materials 216, 218 may include any suitable materials, including, but not limited to, compounds containing waxes, fats, derivatives of waxes and fats, various cellulosic natural and synthetic polymers used either alone or incorporated with various plasticizing agents, and/or mixtures thereof, and/or the like. Non-limiting examples thereof include cellulose acetate phthalate, and fats and waxes associated with various cellulose ethers and esters. Non-limiting examples of polymeric materials suitable for incorporation in the coating material(s) 216, 218 include compounds such as cellulose acetate derivatives, shellac, zein, acrylic resins, ethyl cellulose, hydroxypropylmethylcellulose phthalate, sandarac, modified shellac, and/or mixtures thereof. It is also contemplated that various erosion promoting agents may optionally be incorporated into the coating materials 216, 218 as desired and/or necessitated by a particular end use. These erosion promoting agents include, but are not limited to corn starch, rice starch, potato starch, and other vegetable starches, modified starch, starch derivatives, and/or mixtures thereof, and/or the like. The polymeric materials for incorporation in the coating materials 216, 218 may include suitable carriers, solvents, and/or the like in order to facilitate application and/or deposition.

Polymers, polymeric compositions, and/or mixtures thereof that may be dispensed through an electronic fluid delivery device may be used for one of the coating materials 216, 218 in embodiments of the method and the dose form 116. The nature of the polymer employed may depend on the ultimate end use of the coated dose form 116. For example, in the case of a pharmaceutical preparation, it may be desirable to provide, as a coating, a substantially insoluble major coating compound (e.g. 218 in FIG. 3) with minor portions of a coating (e.g. 216 in FIG. 3) composed of a defined environment soluble polymer (for example, a polymer soluble in the stomach and/or intestinal fluids). For certain pharmaceutical applications and for other purposes, it may be desirable to use a substantially insoluble coating composition with minor portions of water-soluble polymers, polymers soluble in both water and organic solvents, polymers soluble in organic solvents but not water, and/or mixtures thereof.

Non-limitative examples of polymers that are soluble in the stomach include polyvinyl acetal, diethylaminoacetate, polydimethylaminoethylmethacrylate, benzylaminomethylcellulose, diethylaminomethylcellulose, benzylaminoethylhydroxyethylcellulose, cellulose acetate diethylaminoacetate, cellulose acetate dibutylaminohydroxypropyl ether, and/or mixtures thereof.

Examples of water-soluble polymers include, but are not limited to sodium carboxymethylcellulose, methylcellulose (methocel), hydroxymethylcellulose, polyvinyl alcohol, polysaccharide (pullulan), alginate (red algae), gelatin, and/or mixtures thereof.

Further, non-limitative examples of polymers soluble in both water and organic solvents include polyvinyl polyvinylpyrrolidone, pyrrolidone/vinylacetate copolymer, polythylene glycol, hydroxypropylmethylcellulose (HPMC), hydroxypropylcellulose, vinylpyrrolidone/vinylacetatecopolymer, and/or mixtures thereof. Of these, materials such as the pyrrolidone compounds and polysaccharides may be classified as capable of rapid dissolution in a suitable aqueous dissolution environment. Materials such as methyl cellulose, alginate, and hydroxypropyl methylcellulose may be characterized as more slowly dissolving.

Still further, examples of polymers soluble in organic solvents, but not soluble in water include, but are not limited to ethylcellulose, methylvinylpyridine/methylacrylate-methacrylate copolymer, acetylcellulose, nitrocellulose, polyvinylacetate, shellac, and/or mixtures thereof.

It is to be understood that the method and dose form 116 as disclosed herein are not to be limited as to the type of coating materials 216, 218 employed.

In an embodiment, the dose form 116 may optionally include one or more additional coating layer/material(s) (not shown) as desired and/or necessitated for topical use, veterinary applications, and/or the like. It is also contemplated that the additional materials may be classified as suitable and/or safe for human use. It is to be understood that additional coating materials may be applied/deposited as desired and/or necessitated by the process, for example the additional coating material/layer(s) may be applied/deposited sequentially or substantially simultaneously with the quantity of the first and/or second coating materials 216, 218. Further, the additional layer/material(s) may be applied/deposited to targeted locations on the dose form 116 in a manner such that at least a portion of the dispatched additional material(s) is in contiguous relationship with the applied/deposited quantities of the first and/or second coating materials 216, 218 on the dose form 116.

Examples of additional coating layers include, but are not be limited to various enteric polymer-coating compounds. Suitable non-limiting examples of enteric polymers include hydroxypropylmethylcellulose phthalate, cellulose acetate phthalate, methylmethacrylate/methylacrylate copolymers, polyvinyl acetate phthalate, carboxymethylethylethylcellulose, polyvinyl alcohol phthalate, starch acetate phthalate, cellulose acetate succinate, styrene/maleic acid copolymers, and/or mixtures thereof.

It is contemplated that the components (e.g. polymeric components) of the first and second coating materials 216, 218 may be incorporated into suitable respective carrier media/solvent(s). Thus, the respective components may be soluble and/or dispersible within the carrier media/solvent(s). If the component(s) are present in a dispersion, it is contemplated that the diameter of the respective components will be less than about 1 micrometer. If the components are present as dispersed particulate solids, it is contemplated that the respective carrier media/solvent(s) will include appropriate binders and/or the like which will permit the component particles to adhere to one another and/or to the surface 130 of the dose form 116 to which they are applied.

It is to be understood that the carrier media/solvent(s) may be any suitable solvent and/or solubilizing agent capable of delivering the coating material(s) 216, 218 into contact with the surface 130 of the dose form 116. Suitable carrier media/solvent materials are those that will permit or promote adhesion of the coating material(s) 216, 218 to the surface 130 and will permit formation of the desired solid coating layer 214. Desirable carrier media may be those capable of volatilization or promotion of coating layer 214 solidification by other suitable means.

Different carrier media may be used for the different coating materials 216, 218, depending on, among other factors, the size of the respective matrix and islands. Thus, it is contemplated that the carrier media or solvent(s) for the first coating material(s) 216 may differ from those employed with the second coating material(s) 218. Desirable carrier media/solvent material(s) for the second coating material 218 will be one(s) that do not dissolve the applied first coating material 216 upon delivery, and desirable carrier media/solvent material(s) for the first coating material 216 will be one that does not dissolve the applied second coating material 218 upon delivery.

In an embodiment where an additional enteric coating is to be applied subsequent to the application of the first and second coatings 216, 218, it is contemplated that a carrier media for the enteric coating composition will be one compatible with the first and second coating compositions 216, 218. The enteric coating may also include suitable additives as desired and/or necessitated by a particular end use. Non-limiting examples of such additives include materials such as plasticizers, dyes, pigments, and/or mixtures thereof, and/or the like. Non-limiting examples of suitable plasticizers include diethyl phthalate, triethyl citrate, glyceryl triacetate, and/or the like, and/or mixtures thereof.

Referring now to FIG. 4, an alternate embodiment of the dose form 116 having a coating layer 214 composed of a first coating material 216 and a second coating material 218 is depicted. The first coating material 216 is configured in a patterned manner relative to the second coating material 218 such that it presents an identifying indicia.

It is to be understood that either first 216 or second 218 coating material may present the indicia, as long as the material from which the indicia is formed substantially dissolves in contact with the defined environment, so as to create pores 224 through which the active ingredient (a non-limitative embodiment of which is a pharmaceutical agent such as a drug) diffuses in a controlled release fashion from the core of the dose form 116.

In an alternate embodiment, either the first 216 or second 218 coating material may be applied first so as to substantially completely cover the dose form 116. This first applied material should be formed from a material which is substantially insoluble in the defined environment. The other of the second 218 or first 216 coating material may then be applied, in a predetermined configuration, within a carrier which dissolves the first applied material where the first and second applied materials come in contact. As such, both materials directly contact the dose form 116. Upon contact in the defined environment, the second applied material substantially dissolves to create pores 224 through which the active ingredient diffuses in a controlled release fashion from the core of the dose form 116.

This embodiment of the method and dose form 116 may include adding various adjuncts and/or additives (e.g. indicator compounds) as desired and/or as necessary. In one embodiment, it is contemplated that at least one of the first and/or second coating materials 216, 218 may include suitable dyes, pigments, and/or tracers that will impart a suitable color to the desired region 217, 219 of the dose form 116. In this embodiment, it is contemplated that dyes, pigments and/or tracers permit the respective coating materials 216, 218 to contrast one another, either in the visible spectrum and/or in any non-visible spectra in a manner that may be used for inventory control, quality control, and/or the like. The first coating material 216 may be employed to depict identifying indicia, quality control indicia, trademark indicia, and/or the like.

It is to be understood that the first coating material 216 may also have a dissolution characteristic that differs from the second coating material 218. Thus, when exposed to an appropriate dissolving agent, the first coating material 216 selectively dissolves, thus forming the pores 224 that permit access to the internal region 210 of the dose form 116. The size of the pores 224 may be such that the material contained in the dose form 116 may be released in a desired controlled manner. It may be appreciated that application of first and second coating layers 216, 218 having appropriate pigmentation may provide a controlled release aspect while also permitting importation of a suitable control indicia, thereby providing a suitable dose form 116 in an efficient and economical manner without requiring a separate marking step.

By way of example, the first coating material 216 may be suitably pigmented and applied in a desired pattern. The pattern of choice may be identification indicia, lot number, trademark, and/or the like (see FIG. 4). In this non-limitative example, the second coating composition 218 may be applied contiguous thereto to form the unified coating layer 214. The first coating material 216 may have an appropriate dissolution characteristic such that exposure to the dissolution environment will result in the dissolution or erosion of the first coating material 216 as applied/deposited, thereby opening pores 224 for contact with the active material contained in the dose form 116. Until such exposure, the pigmented first coating material 216 may serve as an identification indicia or the like, as previously described.

Another alternate embodiment of the dose form 116 is depicted in FIG. 5. The dose form 116 may also have a suitable coating layer 214 composed of a first coating material 216 and a second coating material 218. The first coating material 216 has a dissolution characteristic that differs from the dissolution characteristic of the second or major coating material 218 such that the coating material 216 selectively dissolves (forming pores 224) when placed in contact with the desired dissolution agent. The first coating material 216 may be patterned at an equatorial axis of the dose form 116. The first coating material 216 is positioned such that upon dissolution, the second coating material 218 will have a region of perforation through which the internal material may migrate. Depending upon the area of perforation, and the material contained in the internal region 210, it is contemplated that migratory action and phenomena, such as the swelling of the interior material, may cause the second coating material 218 to rupture such that the internal material is delivered as desired and/or necessary.

Figure 6:
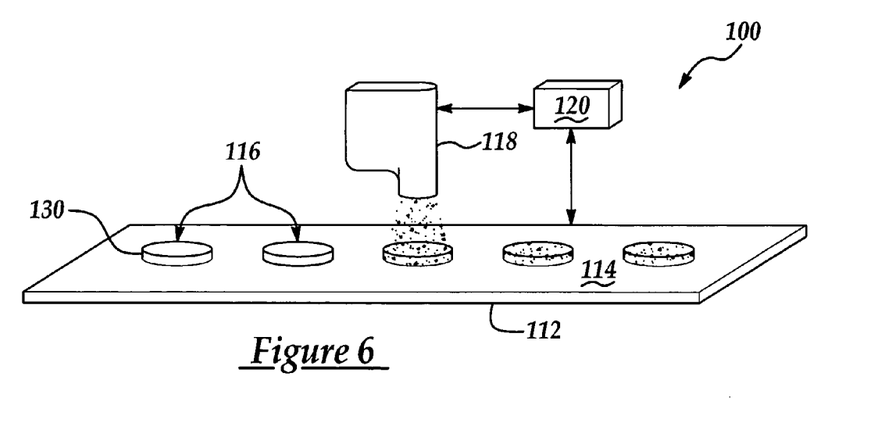
FIG. 6 is a schematic view of an embodiment of an apparatus for implementing an embodiment of the method of the present invention.

Referring now to FIG. 6, a schematic view of an apparatus 100 for producing an embodiment of the dose form 116 is depicted. The apparatus 100 includes a conveying mechanism 112 (one non-limitative example of which is a conveyor belt) having a receiving surface 114 adapted to removably receive a plurality of dose forms 116. The dose forms 116 may be conveyed by conveying mechanism 112 past a suitable electronically controllable fluid delivery device 118. The electronically controllable fluid delivery device 118 may be activated and/or controlled by suitable control electronics 120 located on board and/or integrated into the dose form 116 fabrication assembly 100. The electronically controllable fluid delivery device 118 may be a stationarily mounted device. Alternately, it is contemplated that the fluid delivery device 118 may be configured such that appropriate printheads move relative to the surface 130 of the dose forms 116 to provide appropriate application of the desired coating material(s) 216, 218. Further, the fluid delivery device may optionally include an alignment mechanism confirming alignment of the electronically controllable fluid delivery device 118 and the dose form 116, the alignment mechanism operatively connected to and/or disposed within fluid delivery device 118 and/or conveying mechanism 112.

In this embodiment, the first and second coating materials 216, 218 may be ones that are capable of application and/or deposition from a suitable electronically controllable fluid delivery device 118. By way of example, electronically controllable fluid delivery device 118 may be configured in a manner similar to those found in inkjet delivery devices/technology and, as such, may have mechanisms and devices which control the volume of material ejected, as well as its configuration, trajectory, and/or delivery location. It is to be understood that the electronically controllable fluid delivery device 118 may be configured as a single ejection device or as multiple ejection devices that discharge one or multiple components according to a firing command. The electronically controllable fluid delivery device 118 may also be configured to discharge material(s) from one or multiple chambers. It is contemplated that the devices 118 may be thermally controlled jetting devices and/or controlled by piezoelectric characteristics, and/or the like.

Figure 7:
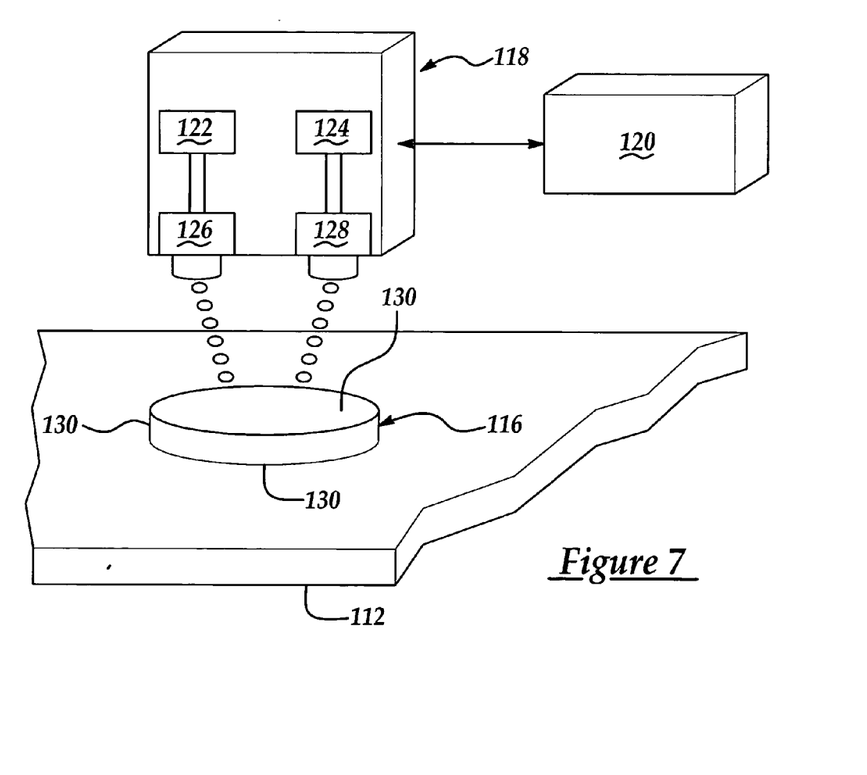
FIG. 7 is a cutaway schematic view of an embodiment of an electronically controllable fluid delivery device of the present invention.

Referring now to FIG. 7, the electronically controllable fluid delivery device 118 may include a plurality of reservoirs 122, 124 in fluid communication with electronically actuated printheads 126, 128, respectively, the printheads 126, 128 configured to dispense controlled amounts of the respective coating materials 216, 218 onto the surface 130 of dose form 116 in a patterned manner.

The dispensing pattern may be controlled by suitable control electronic(s) 120. Where desired and/or necessary, the apparatus 100 may include user interfaces (not shown). It is also contemplated that the pill fabrication apparatus 100 may include suitable dose form 116 indexing means (not shown) to substantially ensure that any/all of the desired surfaces 130 of dose form 116 are suitably coated. Thus, it is contemplated that where desired and/or necessary, the dose forms 116 may be rotated or turned as desired and/or required to ensure appropriate coverage. The dose form 116 fabrication apparatus 100 may also include appropriate quality control devices such as scales, inspection devices, and/or the like.

While several embodiments have been described in detail, it will be apparent to those skilled in the art that the disclosed embodiments may be modified. Therefore, the foregoing description is to be considered exemplary rather than limiting.

What is claimed is:

1. A method for producing a pharmaceutical dose form, comprising the steps of:
   depositing, via an electronically actuated fluid delivery device, a measured quantity of a first coating material directly on a first portion of an external surface of the dose form in a patterned configuration, the first coating material having a dissolution characteristic;
   then depositing, via the electronically actuated fluid delivery device, a measured quantity of a second coating material directly on a second portion of the external surface of the dose form in a patterned configuration in relationship to the first coating material, wherein the second coating material has a dissolution characteristic different from the dissolution characteristic of the first coating material: and
   permitting the first and second coating materials to solidify to form respective distinct regions of a contiguous and continuous coating layer in overlying relationship with at least a portion of the external surface of the dose form.

2. The method as defined in claim 1 wherein exposure to a dissolution environment results in removal of the first coating material and formation of at least one pore in the coating layer.

3. The method as defined in claim 2 wherein the dissolution environment comprises at least one condition occurring in at least one anatomical location of an intended recipient.

4. The method as defined in claim 2 wherein removal of the first coating material results in a porous coating layer overlying the dose form, wherein the at least one pore is positioned in a predetermined patterned manner.

5. The method as defined in claim 1 wherein at least one of the first and second coating materials is ejected in discrete volumes from the electronically controllable fluid delivery device.

6. The method as defined in claim 5 wherein at least one of the first and second coating materials is a liquid applied to a plurality of discrete targeted locations on the dose form.

7. The method as defined in claim 6 wherein at least one of the first and second coating materials contains at least one of a pigment, a dye, and a coloring agent.

8. The method as defined in claim 7 wherein the at least one of the pigment, the dye, and the coloring agent is not visible in visible light.

9. The method as defined in claim 1 wherein at least one of the first and second coating materials contains an active agent.

10. The method as defined in claim 1 wherein each of the first and second coating materials includes a polymeric material comprising at least one of a natural and synthetic polymeric material.

11. The method as defined in claim 10 wherein the at least one of the natural or synthetic polymeric material comprising at least one of polyvinyl acetal, diethylaminoacetate, polydimethylaminoethylmethacrylate, benzylaminomethylcellulose, diethylaminomethylcellulose, benzylaminoethylhydroxyethylcellulose, cellulose acetate diethylaminoacetate, cellulose acetate dibutylaminohydroxypropyl ether, sodium carboxymethylcellulose, methylcellulose (methocel), hydroxymethylcellulose, polyvinyl alcohol, polysaccharide (pullulan), alginate (red algae), gelatin, polyvinyl polyvinylpyrrolidone, pyrrolidone/vinylacetate copolymer, polythylene glycol, hydroxypropylmethylcellulose (HPMC), hydroxypropylcellulose, vinylpyrrolidone/vinylacetatecopolymer, ethylcellulose, methylvinylpyridine/methylacrylatemethacrylate copolymer, acetylcellulose, nitrocellulose, polyvinylacetate, shellac, hydroxypropylmethylcellulose phthalate, cellulose acetate phthalate, methylmethacrylate/methylacrylate copolymers, polyvinyl acetate phthalate, carboxymethylethylethylcellulose, polyvinyl alcohol phthalate, starch acetate phthalate, cellulose acetate succinate, styrene/maleic acid copolymers, and/or mixtures thereof.

12. The method as defined in claim 1 wherein at least one of the first and second coating materials is deposited in discrete volumes, the deposited volumes ranging between about 1 femtoliter and about 500 picoliters.

13. A method for making a dose form containing at least one pharmaceutically active compound therein, the method comprising the steps of:

depositing a first coating material onto a first portion of a dose form surface from an electronically actuated fluid delivery device in a patterned configuration, thereby forming a first distinct region having an inner surface proximate to the surface of the dose form at the first portion, the first coating material comprising a compound having a predetermined solubility characteristic;

depositing a second coating material onto a second portion of the surface of the dose form from the electronically actuated fluid delivery device, thereby forming a second distinct region having an inner surface proximate to the surface of the dose form at the second portion, the second coating material having a coating compound having a predetermined solubility characteristic differing from the first coating material solubility characteristic; and permitting the first and second coating materials to solidify to form a contiguous coating layer overlying the dose form.

14. The method as defined in claim 13 wherein exposure to a dissolution environment results in removal of the first coating material and formation of at least one pore in the coating layer overlying the dose form.

15. The method as defined in claim 14 wherein the dissolution environment is present in at least one anatomical location of an intended patient.

16. The method as defined in claim 13 wherein the first coating material dissolves at a pH between about 1 and about 8.

17. The method as defined in claim 14 wherein the removal of the deposited first coating material results in a porous coating layer overlying the dose form in a patterned manner, wherein a plurality of pores is positioned to provide controlled release of the at least one pharmaceutically active compound contained in the dose form.

18. The method as defined in claim 13 wherein the first coating material is deposited in discrete droplets having a volume ranging between about 1 femtoliter and about 500 picoliters.

19. The method as defined in claim 13 wherein the second coating material is deposited from an electronically activated fluid delivery device in a patterned configuration relative to the deposited first coating material.

20. The method as defined in claim 1 wherein the depositing steps result in a layer of the first coating material formed at the first distinct region non-overlapping a layer of the second coating material formed at the second distinct region.

* * * * *

UNITED STATES PATENT AND TRADEMARK OFFICE
CERTIFICATE OF CORRECTION

| | | |
|---|---|---|
| PATENT NO. | : 8,609,198 B2 | Page 1 of 1 |
| APPLICATION NO. | : 10/896301 | |
| DATED | : December 17, 2013 | |
| INVENTOR(S) | : Iddys D. Figueroa et al. | |

It is certified that error appears in the above-identified patent and that said Letters Patent is hereby corrected as shown below:

In the Specification

In column 6, lines 50-51, delete "polyvinyl polyvinylpyrrolidone" and insert -- polyvinylpyrrolidone --, therefor.

In column 6, lines 51-52, delete "polythylene" and insert -- polyethylene --, therefor.

In the Claims

In column 11, lines 22-23, in Claim 11, delete "polyvinyl polyvinylpyrrolidone" and insert -- polyvinylpyrrolidone --, therefor.

In column 11, lines 23-24, in Claim 11, delete "polythylene" and insert -- polyethylene --, therefor.

In column 12, line 34, in Claim 18, delete "femptoliter" and insert -- femtoliter --, therefor.

Signed and Sealed this
Thirtieth Day of June, 2015

Michelle K. Lee
*Director of the United States Patent and Trademark Office*